United States Patent [19]

Collins et al.

[11] 4,292,252

[45] Sep. 29, 1981

[54] PROCESS FOR PREPARING ORGANOTIN ESTERS

[75] Inventors: John D. Collins, Albrighton; Donald A. Wood, Warley, both of England

[73] Assignee: Tenneco Chemicals Inc., Saddle Brook, N.J.

[21] Appl. No.: 61,262

[22] Filed: Jul. 27, 1979

[30] Foreign Application Priority Data

Jul. 28, 1978 [GB] United Kingdom ............... 31575/78

[51] Int. Cl.$^3$ ................................................ C07F 7/22
[52] U.S. Cl. .................................................. 260/429.7
[58] Field of Search ..................................... 260/429.7

[56] References Cited

U.S. PATENT DOCUMENTS 2,648,650  8/1953  Weinberg et al. ............... 260/429.7
2,832,750  4/1958  Weinberg et al. ............... 260/429.7
3,574,693  4/1971  Fuchsman et al. .............. 260/429.7
4,058,543  11/1977  Mack ........................... 260/429.7 X

*Primary Examiner*—Helen M. S. Sneed
*Attorney, Agent, or Firm*—Frishauf, Holtz, Goodman & Woodward

[57] ABSTRACT

Organotin esters from acid esters of di or poly carboxylic acids are made by mixing base an organotin halide and the acid ester in the presence of water, and reacting to form the organotin ester, the amount of base and acid ester being to provide 0.9–1.3 equivalents and at least 0.9 equivalents respectively per g. atom of halogen in the organotin halide, and the conditions being such as not to cause substantial hydrolysis, and the progressive mixing of base with organotin halide or acid ester being not later than the mixing of organotin halide and acid ester.

23 Claims, No Drawings

PROCESS FOR PREPARING ORGANOTIN ESTERS

This invention relates to a process for preparing organotin compounds, in particular organotin carboxylate esters.

Such esters, as exemplified by dibutyltin bis monoalkyl maleates, are usually prepared by reacting the corresponding hydroxide or oxide, e.g. dibutyltin oxide with a mono ester of a dicarboxylic acid, made by reacting one mole of the dicarboxylic acid anhydride with one mole of alcohol. The organotin oxide or hydroxide is itself made by hydrolysis of the corresponding chloride, e.g. dibutyltin dichloride with aqueous base, e.g. sodium hydroxide solution. The recovery of the oxide, e.g. dibutyltin oxide at the end of the hydrolysis is troublesome, as the oxide, which is insoluble, is difficult to filter and hence difficult to wash to remove byproduct sodium chloride, any excess of base and water. The oxide also needs to be dried. The presence of water or base in the subsequent reaction with the mono ester of the carboxylic acid can cause hydrolysis of the ester and/or anhydride and/or desired reaction product.

We have now found a process for preparing esters directly from the organotin halide without the need for conversion of the halide into oxide.

The present invention provides a process for preparing organotin esters of carboxylic acids, which comprises reacting a base, preferably an aqueous solution of alkali metal hydroxide, an organotin halide of formula $(R')_a SnX_{4-a}$ wherein a is an integer of 1 or 2, X is a chlorine, bromine, or iodine atom, each of R' is an organic group e.g. an organic hydrocarbyl group of 1–20 carbon atoms such as an alkyl group of 1–20 carbon atoms, an alkenyl group of 2–18 carbon atoms, a cycloalkyl group, an aryl group, or an aralkyl group, and a carboxyl compound containing at least one carboxylic acid group and at least one carboxylic ester group of formula $(R^2YOC)_m R^3 (COOH)_n$ wherein m and n are each an integer of 1 to 3, $R^3$ is a single bond or an (m+n) - valent organic group e.g. an organic hydrocarbyl group of 1–20 carbon atoms which may optionally have at least one hydroxyl substituent, e.g. a group derived from a saturated or unsaturated aliphatic hydrocarbon of 1–18 carbon atoms, a hydroxy alkane of 2–18 carbon atoms, a cyclo aliphatic hydrocarbon of 4–15 carbon atoms e.g. 5–7 carbon atoms or an aromatic compound, e.g. of 6–19 carbon atoms, and Y is an oxygen or sulphur atom, and $R^2$ is as defined for R', the reaction carried out in the presence of water and producing an organotin ester with at least one OOCR$^3$COYR$^2$ group attached to a tin atom and preferably two such groups, the amount of said base being to provide 0.9–1.3, e.g. 1.02–1.25 or 1.04–1.12 equivalents per g. atom of halogen bonded to tin in the organotin halide, and the amount of said carboxyl compound being sufficient to replace at least 90% of the halogen atom in the organotin halide, the base, water organotin halide and carboxyl compound being mixed in any order, with the proviso that when base is added progressively to a mixture of all the required organotin halide and all the required carboxyl compound, then at least some base is added to the organotin halide or carboxyl compound before said mixture of all the organotin halide and carboxyl compound is made. When the carboxyl compound is a mono ester mono acid of a dicarboxylic acid of formula $R^3 (COOH)_2$, the organotin ester is substantially of formula $(R')_a Sn (OOC R^3 COYR^2)_b$ wherein a+b=4, and b is an integer of 2 or 3.

In the above compounds the organic groups represented by R', $R^2$ and $R^3$ are stable under the conditions of the reaction, i.e. do not contain reactive groups.

In the above compounds R' may be an alkyl group of 1–18 carbon atoms, e.g. 1–12 carbon atoms, and especially 1–8 carbon atoms, such as methyl, ethyl, propyl, isopropyl, n-butyl, hexyl, n-octyl, iso octyl, 2-ethyl hexyl, decyl, lauryl, cetyl and stearyl, or an alkenyl group of 2–18 carbon atoms, e.g. 2–6 carbons such as vinyl, allyl, and propenyl, a cycloalkyl group, e.g. of 5–7 carbon atoms, such as cyclohexyl or cyclopentyl, an aryl group (and preferably an aromatic hydrocarbyl group), e.g. of 6–19 carbon atoms and preferably 6–12 carbon atoms such as phenyl, tolyl, xylyl and naphthyl or an aralkyl group (preferably an aralkyl hydrocarbyl group), e.g. of 7–19 carbon atoms such as benzyl, β-phenyl-ethyl or benzhydryl. $R^2$ is selected from the same group as R', and may also specifically be an alkoxy or alkylthio-alkyl group each of 2–18 carbon atoms, e.g. 2–10 carbon atoms especially those with 1–6 carbon atoms in the alkoxy (or alkylthio) and alkyl groups such as the butoxethyl or butyl thioethyl groups. Alternatively $R^2$ may be an alkan-on-yl group such as a propan-2-on-1-yl group. Most preferably R' is an alkyl group of 1–10 in particular 4–10 carbon atoms, e.g. methyl, n butyl or octyl, or a cyclohexyl or phenyl group. Most preferably $R^2$ is an alkyl group of 1–20 carbon atoms, e.g. 4–18 e.g. 6–10 or 3–10 especially 4–8 carbon atoms or a cyclohexyl group. It is not essential that all the R' groups in the organotin starting material are the same, so that for example, mixed organotin compounds may be used, e.g. butyloctyltin compounds. Similarly, different $R^2$ groups may be used, as for example when $R^2OH$ represents an "OXO" alcohol of, e.g. 8 or 12–16 carbon atoms. Also different X groups may be present in the same molecule.

While in the carboxyl compound of formula $(R^2YOC)_m R^3 (COOH)_n$ m and n are each 1–3, it is preferred that the sum is 2–4 with n 1 or 2 m 1–3; particularly preferred values of m and n are 1 each.

When the carboxyl ester/acid compound is based on a dicarboxylic acid, (m and n are each 1) $R^3$ may be an alkylene group of 1–18 carbon atoms, preferably 2–10 carbon atoms, such as methylene, ethylene, 1,4 butylene, 1,8 octylene, or an alkenylene group of 2–18 carbon atoms, preferably 2–10 carbon atoms such as —CH=CH—, 1,2 -prop-2,3-enylene, (as in itaconic acid) 1,2 prop-1,2-enylene, (as in malic acid), or a 1,2-bis hydroxylethylene 1,2 group (as in tartaric acid), a cycloalkylene group, e.g. of 5–7 carbon atoms such as 1,4-cyclohexylene, an arylene group (preferably a divalent aromatic hydrocarbyl group), e.g. of 6–19 carbon atoms, especially 6–12 carbon atoms, such as phenylene or 1,2-naphthylene. Most preferably $R^3$ is group of formula —CH=CH—, in the cis form (based on maleic acid) or trans form (as in fumaric acid), or an ethylene group $R^3$ may also be an organic group with 2 or more fused rings, especially bridged rings such as the groups attached to an anhydride group obtained by reacting maleic anhydride with conjugated dienes such as cyclopentadiene and halogenated derivatives thereof, or aliphatic conjugated dienes, e.g. to make the acid $R^3 (COOH)_2$ an alkenyl succinic acid. $R^3$ may also be a single bond as in oxalic acid.

When the carboxyl compound is based on an acid with (m+n) carboxyl groups in which the total of m and n is an integer of 3–6, $R^3$ may be an (m+n) valent group based on an alkane of 1–18 carbon atoms, preferably 2–10 carbon atoms, such as propane (as in tricarballylic acid), or a hydroxy substituted derivative of such an alkane, such as propane (as in citric acid), or an alkene of 2–18 carbon atoms, e.g. 2–10 carbon atoms or a cycloalkane, e.g. of 5–7 carbon atoms, or an aromatic compound (e.g. an aromatic hydrocarbon) of 6–19 carbon atoms, especially 6–13 carbon atoms such as benzene (as in mellitic, pyromellitic, benzene-1,2,4,5-tetracarboxylic acid and trimellitic acids). Again bridged polycyclic groups, the nuclei from maleic anhydride/conjugated diene condensation products, may represent $R^3$.

Preferably the carboxylic acid $R^3(COOH)_{m+n}$ is one with a first acid dissociation constant such that its $pK_a$ is not more than 3.2 e.g. 1–3.2, preferably 1–2.5 and especially 1–2 such as 1.5–2. Such acids are to be found among di and tri carboxylic acids, in which $R^3$ is an aliphatic hydrocarbyl group of 1–3 carbon atoms, optionally substituted with 1–3 hydroxyl groups, as in maletic, dihydroxymalic, hydroxytartaric, malonic, fumaric, lactic, tartaric, or an aromatic hydrocarbyl group of 6–8 carbon atoms as in phthalic acid, or in which $R^3$ is a single bond as in oxalic acid.

The reaction is carried out in the presence of base, which is preferably water soluble. It may be inorganic as in the hydroxides, carbonates or bicarbonates of ammonia, alkali metals such as sodium or potassium, alkaline earth metals such as calcium e.g. as CaO, or may be a quaternary organic hydroxide, carbonate or bicarbonate, e.g. a tetraalkyl ammonium compound in which each alkyl has 1–8 carbon atoms in each alkyl group such as tetramethyl-, tetraethyl-, tetra butyl- or tetraoctyl ammonium. Preferably the base is water soluble and a hydroxide, carbonate or bicarbonate of an alkali metal group and especially the amount of base is 90–130%, e.g. 95–125% or 106–110% the amount needed to neutralize the number of moles of hydrogen halide produced in the reaction.

The molar proportion of carboxyl compound to organotin starting materials depends on the number of halogen atoms in the organotin halide and the number of free carboxylic acid groups on the carboxyl compound and desired in the product, but is usually such that for each halogen in the organotin there is 0.9–1.3, preferably 0.98–1.2 (especially at least one) acid equivalent of carboxyl compound per halogen atom. Thus when, as in preferred, a monoester of a dicarboxylic acid is reacted with the organotin halide, there is preferably 0.98–1.2, e.g. about 1 molecule of carboxyl compound per atom of halogen; thus preferably 1 mole of diorganotin dihalide is reacted with 1.95–2.4 moles (e.g. about 2 moles) of a monoester of a dicarboxylic acid and 1.9–2.5 equivalents of base e.g. an alkali metal carbonate or hydroxide. The base usually provides 0.9–1.3 e.g. 1.0–1.3 such as 1.02–1.2 equivalents per equivalent of carboxyl group within the broad confines of the range of amount of base to halogen. Thus in the process there may be used amounts of base, monoacid monoester carboxyl compound and organotin halide such as to give 1 molar proportion of organotin halide containing (4-a) g. atoms of halogen, and (4-a) (0.9–1.3) proportions of monoacid ester salt (from the base and said acid ester) and up to 0.25 (4-a) equivalent proportions of base, the total of molar or atomic proportions or cation in the salt and in the base if present being (4-a) (0.9–1.3). Preferably said proportions of organotin halide to salt to base are 1:(4-a) (0.97–1.25):0–0.2 (4-a). Hence for a monoacid monoester such as a maleate half ester, and a diorganotin dihalide said proportions would be 1:1.8–2.6:0–0.5, preferably 1:1.95–2.5:0–0.4, with the total proportion of cation being 2.02–2.5.

The reaction between the organotin halide, the carboxyl compound and base e.g. hydroxide is carried out by mixing or premixing the organotin halide and carboxyl compound, water and base in the desired proportions in any order with addition of any of the reagents to one or more of the others stepwise but with the proviso given above which requires that all the base is not added progressively to a mixture of all the organotin halide and all the carboxyl compound. Thus when base is added in a batch process to a preformed mixture comprising organotin halide and carboxyl compound, then at least some of the totally required amount of base shall already be present before the last of the totally required amount of the organotin halide or carboxyl compound is added. The water may be added separately or mixed first with one or more of the reactants especially the base. All the carboxyl compound may be added to a mixture of all the base and all the organotin halide, or all the organotin halide may be added to a mixture of all the base and all the carboxyl compound, or some of the base (e.g. 10–98%, preferably 90–98% of the totally required amount and especially 0.9–1.0 equivalents per g. atom of halogen in the halide) may be mixed with carboxyl compound, and then organotin halide added, and finally the rest of the base may be added, or, the organotin halide mixed with some of the base (e.g. 10–98% preferably 90–98% of the totally required amount) before addition of the carboxyl compound and the rest of the base. Finally all the base, all the carboxyl compound, all the water and all the organotin halide may be mixed continuously and simultaneously e.g. metered in the appropriate proportion into the reaction vessel, or, in a continuous process metered in the appropriate proportion into either a reaction line, or into a reaction vessel, from either of which reaction product is continuously removed after a short residence time e.g. 5–20 mins. The 4 components may each be metered in separately so that they first meet simultaneously, or any combination of the reactants may be mixed first and the rest added separately but simultaneously. Thus water and base may be mixed first and the aqueous base, organotin halide and carboxyl compound mixed simultaneously. Alternatively in a continuous process the mixture of aqueous base can be added continuously to a preformed mixture of all the organotin and carboxyl compound, said mixture being preferably in the absence of base or salt of said base and carboxyl compound; any extra water may be added separately. When the base and carboxyl compound are present together in the absence of organotin halide, the conditions are such as to minimize hydrolysis as preferably are the conditions when the base and organotin halide are present in the absence of carboxyl compound. Thus in the former case, until all the organotin halide has been added to the mixture of base, carboxyl compound and water, the temperature is preferably less than 45° C. e.g. less than 40° C., and the temperature and time from first contact of base and carboxyl compound to the end of the addition of organotin halide is such as to result in less than 10% hydrolysis of the carboxyl compound.

The mixing of base, acid ester carboxyl compound and organotin halide and the reaction are carried out under conditions of time, temperature and proportions of the three reactants that there is little or no e.g. substantially no hydrolysis of the organotin product. Increased hydrolysis with any particular acid ester results from increasing the time of addition or reaction, increasing the temperature of the addition or reaction, increasing the proportion of base to acid ester or organotin chloride. Reducing the alkyl chain length of the alkyl group of an alkyl ester or replacing it by a benzyl group also increases the likelihood of hydrolysis as does inceasing the basic strength of the base and/or increasing the concentration of base in the reaction mixture, and/or increasing the atomic weight of the halogen and/or increasing the first acid dissociation constant of the acid $R_3(COOH)_{m+n}$ (i.e. decreasing the $pK_a$).

The reaction is usually carried out at below the boiling point of the mixture but while reaction temperature of $-30°$ C. to boiling point may be used, addition and reaction temperatures of $-10°$ C. to 70° C. e.g. 0–50° C. are often desirable. Total addition and reaction times of 1 minute to 24 hours e.g. addition times of 5 mins. to 2 hrs. are often suitable. The total reaction is usually carried out for a time and at a temperature, such that not more than 10% of the ester is hydrolysed. After the addition is complete, the reaction mixture produced may be treated for up to 5 hrs., e.g. 0.5–2 hrs. further at up to 70° C. The pH of the reaction mixture after the addition but before the further heating (if any) is preferably 1.5–7, e.g. 2–4.5 such as 3–4.

With dialkyltin dichlorides and alkyl maleate half esters, especially those of 4–10 carbon atoms, total reaction times of 5 mins. to 5 hrs., at $-10°$ to $+70°$ C., e.g. 30 mins. to 2 hrs. at $-10°$ to $+60°$ C. have been found suitable. When the base is mixed with the carboxyl compound before the latter and organotin halide meet, then the reaction temperature until all of the base, carboxyl compound and organotin halide are present is preferably less than 45° C. e.g. less than 25° C.

The addition and reaction are preferably carried out under conditions such that the organotin product at the end of the reaction contains a weight ratio of chlorine to tin of less than 1:8 e.g. 1:600 to 1:8 preferably 1:600 to 1:15 and especially 1:600 to 1:32 such as 1:600 to 1:100 and corresponding weight ratios of the same atom ratio as above when the halogen is bromine or iodine. These conditions especially apply to reaction of dialkyltin dichlorides, e.g. of 2–24 e.g. 6–16 carbon atoms such as dibutyl dichloride, and monoalkyl maleates, with 3–12 carbon atoms, particularly 6–10 carbon atoms in the alkyl group in the ester, the organotin product at the end of the reaction preferably containing less than 2% Cl, e.g. less than 1.2% Cl and preferably less than 0.5 Cl; chlorine contents of 0.05–0.15% with dibutyl bis (octyl maleate) isomers are highly advantageous.

Each of the organotin halide and carboxyl compound may be dissolved in an inert water immiscible liquid solvent such as an aliphatic or cyclo aliphatic hydrocarbon of 5–12 carbon atoms such as cyclohexane or "petroleum ether" of boiling point in the range of 40°–180° C., preferably 60°–80°, 80°–100° or 100°–120° or a liquid aromatic hydrocarbon, e.g. of 6–9 carbon atoms such as benzene, toluene or xylene; the solvent is one which dissolves the acid ester and organotin ester. However, preferably an inert water immiscible liquid solvent, in particular one capable of forming an azeotrope with water, is absent so the reaction is preferably carried out in the absence of any organic solvent, though the organotin halide and carboxyl compound may be dispersed in water. The ratio of the number of equivalents of base e.g. hydroxide to total moles of water added is usually 0.001–0.5:1 0.01–0.2:1, e.g. 0.03:1 to 0.08:1. Preferably the reaction is carried out in the substantial absence of any added compound of formula $R^2YH$, e.g. an alcohol, e.g. with less than 10 mole% based on the number of g. atoms of halogen in the organotin halide.

The addition and reaction are carried out with agitation of the reactants and water.

At the end of the reaction there are produced 2 layers, one comprising the organotin ester product and the other an aqueous layer; the organotin ester layer is separated from the aqueous layer. Adjustment of the temperature at the end of the reaction to 40°–70° C. often aids separation of the layers. In addition or alternatively, in order to improve the separation between the layers, the reaction liquid may be extracted with an inert water immiscible liquid solvent such as hydrocarbon such as paraffin or petroleum ether or aromatic hydrocarbon such as benzene, toluene or xylene, or a chlorinated hydrocarbon or an ether. The extract may be separated and the organotin product recovered by evaporation. If a water immiscible solvent has been used in the reaction, then at the end the organic extract layer is separated from the aqueous layer.

Preferably as soon as possible after the reaction is complete, the 2 layers are separated, and advantageously the layer containing the organotin ester is washed with water, before being dried e.g. under vacuum.

The processes of separation into 2 liquid layers and washing if performed can be carried out continuously e.g. in mixer settlers or, in the case of washing in scrub columns followed by settlers. The final evaporation can also be performed batch wise or continuously.

In a particularly preferred process, the aqueous solution of base, e.g. an alkali metal hydroxide, a carboxyl compound of formula $R^2OOC\ R^3COOH$ where $R^2$ and $R^3$ are as defined above, but preferably $R^2$ is an alkyl group of 1–20 carbon atoms and $R^3$ is a group of formula cis $-CH=CH-$, and a diorganotin chloride of formula $R_2'SnCl_2$ where $R'$ is defined above but is preferably an alkyl group of 1–10 e.g. 4–10 carbon atoms, are reacted in the presence of water, the molar ratio of carboxyl compound to organotin halide being 1.9:1 to 2.2:1 (e.g. about 2:1) preferably at a temperature of $-10°$ C. to $+70°$ C. e.g. $-10°$ C. to $+55°$ C., the number of equivalents of the hydroxide being between 101–120%, e.g. 102–116% especially 104–112% of the number of g. atoms of chlorine in the organotin chloride, to form an organotin ester, e.g. of formula $R_2'Sn(OOC\ R^3COOR^2)_2$ substantially free of organotin compounds containing Sn-Cl bonds (e.g. less than 1.5% Cl particularly less than 1.2% Cl), the addition of the reactants and subsequent reaction being carried out at less than the boiling point of the reaction mixture, e.g. at 0°–70° C. to produce two liquid layers, an organotin layer and an aqueous layer. Especially in this preferred process the aqueous hydroxide may be mixed with the carboxyl compound and water, and then the diorganotin chloride is added, or alternatively in a continuous process said aqueous solution of hydroxide, water said maleate ester and diorganotin chloride are mixed continuously or alternatively in a continuous process said aqueous solution of hydroxide is added continuously to a preformed mixture of said ester and diorganotin chloride usually in the presence of water.

The organotin esters (and thio esters) prepared by the process of this invention may be used as heat stabilizers for halogen containing polymers; the esters (and thio esters) may be added to the polymers in amounts of 0.1–10% by weight of polymer. The organotin esters may be used as sole stabilizers or may be mixed with other organotin compounds or extended with the unreacted acid ester of alkyl alkanoates with 1–8 carbons in the alkyl group and 6–20 carbons in the alkanoate. The polymers may be homopolymers or copolymers of vinyl chloride or vinlyidene chloride, or copolymers or either or both of these with other oleofinic copolymerizable monomers, e.g. vinyl acetate. The polymers contain at least 40% by weight of chlorine.

The invention is illustrated in the following Examples.

EXAMPLE 1

Aqueous sodium hydroxide solution (19.3 g. NaOH 0.482 mold, in 143 ml water) was added at 5° C. with cooling to stirred monoisooctyl maleate (100 g. 0.438 mole) over 3 mins. The mixture obtained was kept at +5° C. and with agitation molten dibutyltin dichloride (66.7 g., 0.219 mole) was added dropwise over 15 mins. The reaction mixture was than stirred further for 45 mins. at 20° C. and heated to 40°–45° C. over 30 mins. Two liquid phases appeared and were separated, the lower organic phase containing organotin compound being washed with water at 40°–45° C. over 30 mins. The phases were separated and the organic phase dried by heating under water pump vacuum to 100° C. There remained as residue crude dibutyltin (bis isooctyl maleate) in 94.3% weight yield; the crude product contained 0.07% Cl.

EXAMPLE 2

Aqueous sodium hydroxide solution (19.3 g. 0.482 mole in 55 ml water) was added at 3° C. with cooling to a stirred suspension of dibutyltin dichloride (66.7 g. 0.219 mole) in water (88 ml) over 5 mins. The mixture obtained was cooled to 3° C. and with stirring monoisooctyl maleate (100 g. 0.438 mole) was added over 35 mins. and stirred for a further hour at 3° C. The reaction mixture was stirred and heated to 40°–45° C. over 30 mins. Two liquid phases appeared and were separated and the organic phase was washed with water at 40°–45° C. for 30 mins and then evaporated as in Example 1. The crude dibutyltin bis (isooctyl maleate) was obtained in 94.2% yield and contained 0.16% Cl.

EXAMPLE 3

Aqueous sodium hydroxide solution (17.5 g. 0.438 mole in 133 ml water) was added dropwise to monoisooctyl maleate (100 g. 0.438 mole) over 20 mins. with stirring, maintaining the temperature at 45° C. To the mixture obtained was added molten dibutyltin dichloride (66.7 g. 0.219 mole) dropwise over 20 mins. at 40°–45° C. followed by addition of more of said sodium hydroxide solution (1.4 g. 0.034 mole, in 10 ml water, making 0.472 mole in total). The reaction mixture was then heated for 1 hr. at 40°–45° C. with stirring. The two phases were separated and the organic phase washed and evaporated as in Examples 1 and 2. Crude dibutyltin bis (isooctyl maleate) was obtained in 95.7% weight yield and contained 0.13% Cl.

EXAMPLE 4

Into a 5 necked container fitted with a stirrer and kept in an ice/salt bath were passed simultaneously over 30 mins. at uniform rate 4 streams. 47% by weight aqueous sodium hydroxide solution (total weight 18.9 g. NaOH, 0.472 moles 21 g. water), water (122 g.), molten dibutyltin dichloride (total weight 66.7 g. 0.219 moles) and monoisooctyl maleate (total weight 100 g. 0.438 moles). The temperature of the stirred reaction mixture during the addition was kept at 18°–22° C. After the addition, the mixture was stirred for 15 mins. at 18° C., then heated up to 45°–50° C. over 20 mins. The two liquid phases obtained were separated and the organotin layer washed with water as in Ex. 1–3. The washed organotin layer was dried under water pump vacuum to 100° C. to leave crude dibutyltin bis (isooctyl maleate) in 95.8% weight yield and containing 0.08% Cl.

EXAMPLE 5

Di butyl tin dichloride (152 g. 0.5 mole) and mono iso octyl maleate (228 g 1.0 mole) were mixed together until a homogeneous mixture (335 ml) was obtained. An aqueous base solution (335 ml) was made from sodium hydroxide (44 g, 1.1 mole) and water (334 ml). The homogenous mixture and aqueous base solution were passed each at 4 ml/min into a stirred 250 ml vessel. The temperature rose initially and was kept at a maximum of 50° C. by cooling. After 10 mins, when the vessel was about one third full, the contents of the vessel were slowly drained into a similar washing vessel containing water (200 ml); the flow rate out of the reaction vessel was adjusted to keep a constant level in that vessel. The contact in the washing vessel produced an upper aqueous layer, which was periodically replenished with fresh water, and a lower organic layer which was passed through a falling film evaporator maintained at 100° C. under 25 mm Hg pressure; again the flow to the evaporator was adjusted to keep a constant level in the washing vessel. The product from the evaporator was filtered and analyzed. Yield 313.7 g, (91.3%) Analysis Cl 0.09% with a similar IR spectrum to that obtained in the other Examples. Once the reaction had been operated for about 30 mins, the temperature of the contents of the reaction vessel was about 30°–35° C.

We claim:

1. A process for preparing organotin esters of carboxylic acids, which comprises reacting a base, an organotin halide of formula $(R^1)_a SnX_{4-a}$ wherein a is an integer of 1 or 2, X is a chlorine, bromine or iodine atom, and each of $R^1$ is an organic group, and a carboxyl compound containing at least one carboxylic acid group and at least one carboxylic ester group of formula $(R^2YOC)_m R^3(COOH)_n$ wherein m and n are each an integer of 1 to 3, $R^3$ is a single bond or an (m+n) - valent organic group, and Y is an oxygen or sulphur atom, and $R^2$ is as defined for $R^1$, the reaction being carried out in the presence of water and producing an organotin ester with at least one $OOCR^3COYR^2$ group attached to a tin atom, the amount of said base being to provide 0.9–1.3 equivalents per g. atom of halogen bonded to tin in the organotin halide, and the amount of said carboxyl compound being sufficient to replace at least 90% of the halogen atom in the organotin halide, the base, organotin halide and carboxyl compound being mixed in any order; provided, however, that when base is added progressively to a batch mixture of all the required organotin halide and all the required carboxyl compound, then at least some of the base is added to the organotin halide or to the carboxyl compound before all of the organotin halide and all of the carboxyl compound are admixed to form said mixture.

2. A process according to claim 1 wherein the carboxyl compound is a monoacid monoester of formula $R^2YOCR^3COOH$.

3. A process according to claim 2 wherein the proportions of base, carboxyl compound and organotin halide are such as to give 1 molar proportion of organotin halide containing (4-a) g. atoms of halogen and (4-a) (0.9-1.3) equiv. proportions of monoacid ester salt from the base and said carboxyl compound and up to 0.25 (4-a) equivalent proportions of base, the total of molar or atomic proportions of cation in the salt and in the base, if present, being (4-a) (0.9-1.3).

4. A process according to claim 1 wherein the carboxyl compound is derived from an acid $R(COOH)_{m+n}$, for which the first acid dissociation constant ($pK_a$) is 1-2.5.

5. A process according to claim 1 wherein all the base and all the carboxyl compound are mixed in the presence of water and then the organotin halide is added.

6. A process according to claim 5 wherein before all the organotin halide has been added, the temperature is less than 40° C. and there is less than 10% hydrolysis of the carboxyl compound.

7. A process according to claim 1 wherein the base and organotin halide are mixed in the presence of water and then the carboxyl compound is added.

8. A process according to claim 1 wherein in a continuous process aqueous base, organotin halide and carboxyl compound are mixed continuously.

9. A process according to claim 1 wherein in a continuous process, aqueous base is added continuously to a reaction vessel and a preformed mixture of organotin halide and carboxyl compound is also added continuously to said reaction vessel to continuously form a reaction product containing said organotin ester of carboxyl acid which is continuously removed.

10. A process according to any one of claims 1, 8 and 9 wherein the amount of base is such as to provide 1.02-1.25 equivalents per g. atom of halogen in the organotin halide.

11. A process according to claim 10 wherein the base provides 1.04-1.12 equivalents per g. atom of halogen.

12. A process according to claim 1 wherein the organotin halide is of formula $R'_2SnCl_2$, wherein $R'$ is as defined in claim 1.

13. A process according to claim 12 wherein the organotin halide is a dialkyltin dichloride in which the alkyl group contains 1-8 carbon atoms.

14. A process according to claim 4 wherein the carboxyl compound is a maleate half ester of formula $R^2OOC\ CH=CH-COOH$ wherein $R^2$ is an alkyl group of 1 to 20 carbon atoms or a cyclohexyl group.

15. A process according to claim 14 wherein the maleate half ester is of formula $R^2OOC\ CH=CHCOOH$, wherein $R^2$ is an alkyl group of 4-10 carbon atoms or a cyclohexyl group.

16. A process according to claim 15 wherein the maleate half ester is a mono octyl maleate isomer.

17. A process according to claim 1 wherein the reaction is carried out at less than the boiling point of the mixture to produce 2 liquid layers, an organotin layer and an aqueous layer.

18. A process according to claim 17 wherein the reaction is carried out at $-10°$ to $+60°$ C.

19. A process according to claim 1 wherein an aqueous solution of an alkali metal hydroxide reacts with an organotin halide of formula $R'_2SnCl_2$ and a maleate half ester of formula $R^2OOC\ CH=CHCOOH$ wherein $R^2$ is an alkyl group of 1 to 20 carbon atoms or a cyclohexyl group.

20. A process according to claim 19 wherein said aqueous solution of an alkali metal hydroxide, said maleate ester and a diorganotin chloride of formula $R_2'SnCl_2$ wherein $R'$ is an alkyl group of 4-10 carbon atoms or a cyclohexyl group, are reacted in the presence of water, the molar ratio of ester to organotin chloride being 1.9:1 to 2.2:1, the number of equivalents of the hydroxide being between 104-112% of the number of g. atoms of chlorine, to form an organotin ester of formula $R_2'Sn\ (OOC\ CH=CH\ COOR^2)_2$ containing less than 1.2% Cl and the reaction is carried out at less than the boiling point of the mixture to produce 2 liquid layers, an organotin layer and an aqueous layer.

21. A process according to claim 20 wherein said aqueous solution of hydroxide is mixed with said maleate ester and water, and then said diorganotin chloride is added.

22. A process according to claim 20 wherein in a continuous process said hydroxide water, said maleate ester and diorganotin chloride are mixed continuously.

23. A process according to claim 20 wherein in a continuous process, said aqueous solution of hydroxide is added continuously to a reaction vessel and a preformed mixture of said ester and diorganotin chloride is also added continuously to said reaction vessel to continuously form a reaction product containing said organotin ester of carboxyl acid which is continuously removed.

* * * * *